United States Patent
Li et al.

(10) Patent No.: US 12,268,504 B2
(45) Date of Patent: Apr. 8, 2025

(54) COGNITIVE DISORDER HUMAN-COMPUTER INTERACTION METHOD AND SYSTEM BASED ON EMOTION MONITORING

(71) Applicant: BEIJING WISPIRIT TECHNOLOGY CO., LTD, Beijing (CN)

(72) Inventors: Shiyi Li, Beijing (CN); Yan Xu, Beijing (CN); Zhujiang Ma, Beijing (CN); Xiaoyi Wang, Beijing (CN)

(73) Assignee: BEIJING WISPIRIT TECHNOLOGY CO., LTD, Beijing (CN)

( * ) Notice: Subject to any disclaimer, the term of this patent is extended or adjusted under 35 U.S.C. 154(b) by 85 days.

(21) Appl. No.: 18/148,825

(22) Filed: Dec. 30, 2022

(65) Prior Publication Data

US 2023/0148925 A1 May 18, 2023

Related U.S. Application Data

(63) Continuation of application No. PCT/CN2022/120987, filed on Sep. 23, 2022.

(51) Int. Cl.
*A61B 5/16* (2006.01)
*A61B 5/00* (2006.01)
*G06F 3/01* (2006.01)
*G06V 40/16* (2022.01)

(52) U.S. Cl.
CPC ............ *A61B 5/165* (2013.01); *A61B 5/0077* (2013.01); *G06F 3/012* (2013.01); *G06F 2203/011* (2013.01); *G06V 40/174* (2022.01)

(58) Field of Classification Search
CPC ........ A61B 5/165; A61B 5/0077; G06F 3/012
See application file for complete search history.

(56) References Cited

FOREIGN PATENT DOCUMENTS

CN 113157371 A * 7/2021

* cited by examiner

*Primary Examiner* — Kesha Frisby
(74) *Attorney, Agent, or Firm* — George Guosheng Wang; Upstream Research and Patent LLC

(57) ABSTRACT

Disclosed are a cognitive disorder human-computer interaction method and system based on emotion monitoring. The human-computer interaction method includes the following steps: obtaining a cognitive ability level of a user; generating a human-computer interaction scheme according to the cognitive ability level; generating an $N^{th}$ human-computer interaction task according to the human-computer interaction scheme; carrying out emotion monitoring on the performance of the user in the $N^{th}$ human-computer interaction task, and returning to the previous step of generating an $N^{th}$ human-computer interaction task according to the human-computer interaction scheme, whereby N=N+1 until all tasks in the human-computer interaction scheme are completed; and carrying out, in the process of human-computer interaction, a relaxed human-computer interaction between two adjacent human-computer interaction tasks, and selecting a task type of the relaxed human-computer interaction according to an emotion comprehensive index of the user in the previous human-computer interaction task.

8 Claims, 11 Drawing Sheets

COGNITIVE DISORDER HUMAN-COMPUTER INTERACTION METHOD AND SYSTEM BASED ON EMOTION MONITORING

BACKGROUND

Technical Field

The present disclosure relates to a cognitive disorder human-computer interaction method based on emotion monitoring, and also relates to a corresponding cognitive disorder human-computer interaction system, which fall within the technical field of human-computer interaction.

Related Art

Cognition refers to an ability of the human brain to change into cognition and learned knowledge by processing inner activities after contacting with external information or things, that is, to learn new things, acquire knowledge and apply the learned knowledge. Cognitive functions include memory, comprehension, computing power, language abilities, visual space abilities, judgment and comprehension abilities, etc. If one or more of the above-mentioned cognitive functions are impaired, the impairment may be considered as a cognitive dysfunction. The cognitive dysfunction not only affects living abilities, but also affects social abilities.

According to statistics, 10%-20% of the elderly over 65 years old have mild cognitive impairment. The study found that about 10% of the patients with mild cognitive impairment are deteriorated to cognitive disorders after 1 year. The cognitive disorders are also known as senile dementia, brain degeneration, and dementia. The cognitive disorders have symptoms such as memory decline, decreased thinking ability, influence on communication with family, and frequent emotion instability. The patients with serious cognitive disorders will be disabled in self-care.

The cognitive dysfunction, if not prevented, will go through the process from mild cognitive impairment to cognitive disorder, and cognitive training is an effective way to improve brain cognitive dysfunction, and is one of the commonly used cognitive rehabilitation treatment means. In addition to the traditional artificial cognitive training, the combination of computer technology with cognitive rehabilitation training can effectively improve the efficiency of cognitive training, and training data results can be managed in a unified manner, thereby facilitating view and analysis.

However, in the existing cognitive disorder evaluation schemes, users cannot evaluate or intervene in the influence of real-time emotion state fluctuations of users on training effects in the process of evaluation and training.

SUMMARY

The primary technical problem to be solved by the present disclosure is to provide a cognitive disorder human-computer interaction method based on emotion monitoring, so as to improve the effect of cognitive disorder human-computer interaction.

Another technical problem to be solved by the present disclosure is to provide a cognitive disorder human-computer interaction system based on emotion monitoring.

To achieve the foregoing technical objectives, the present disclosure uses the following technical solutions:

According to a first aspect of embodiments of the present disclosure, a cognitive disorder human-computer interaction method based on emotion monitoring is provided, including the following steps:

obtaining a cognitive ability level of a user;

generating a human-computer interaction scheme according to the cognitive ability level;

generating an $N^{th}$ human-computer interaction task according to the human-computer interaction scheme, N being a positive integer; and carrying out emotion monitoring on the performance of the user in the $N^{th}$ human-computer interaction task, and returning to the previous step of generating an $N^{th}$ human-computer interaction task according to the human-computer interaction scheme, whereby N=N+1 until all tasks in the human-computer interaction scheme are completed.

Preferably, in the process of human-computer interaction, a relaxed human-computer interaction is carried out between two adjacent human-computer interaction tasks, and a task type of the relaxed human-computer interaction is selected according to an emotion comprehensive index of the user in the previous human-computer interaction task.

When the emotion comprehensive index is positive, a human-computer interaction task of a high strength challenge class is selected, when the emotion comprehensive index is negative, a human-computer interaction task of a high relaxation and stress relief class is selected, and when the emotion comprehensive index is neutral, a human-computer interaction task is randomly selected.

Preferably, when the user completes the relaxed human-computer interaction, the next human-computer interaction task is pushed according to a human-computer interaction result of the previous human-computer interaction task and the emotion comprehensive index of the user after the relaxed human-computer interaction.

Preferably, the human-computer interaction result is divided into good, moderate and poor, and the emotion comprehensive index is divided into positive, normal and negative.

When the human-computer interaction result is good, task pushing is successively carried out according to upgrade, upgrade, and reduce pushing and upgrade in the order of the emotion comprehensive index being positive, normal and negative.

When the human-computer interaction result is moderate, task pushing is successively carried out according to increase pushing, maintain, and reduce pushing in the order of the emotion comprehensive index being positive, normal and negative.

When the human-computer interaction result is poor, task pushing is successively carried out according to increase pushing and degrade, degrade, and degrade in the order of the emotion comprehensive index being positive, normal and negative.

Preferably, acquiring an emotion comprehensive index of a user specifically includes:

acquiring expression information of the user in each collection time period;

acquiring expression features in the expression information, and comparing the expression features with an Asian face database so as to obtain proportions of a positive emotion, a negative emotion and a neutral emotion in the expression information, the emotion with the maximum proportion being a current emotion of the user;

determining proportions of positive emotions, negative emotions and neutral emotions in all the current emotions of the user in the whole process of human-computer interaction;

acquiring a current emotion state of the user based on the proportions of the positive emotions, the negative emotions and the neutral emotions in all the current emotions of the user;

acquiring an emotion change state of the user based on an emotion proportion and a time change in each collection time period;

acquiring an emotion fluctuation state of the user based on the emotion proportion and the time change in each collection time period; and obtaining the emotion comprehensive index of the user according to at least two of the current emotion state, the emotion change state and the emotion fluctuation state.

Preferably, the acquiring a current emotion state of the user based on the proportions of the positive emotions, the negative emotions and the neutral emotions in all the current emotions of the user specifically includes:

when the proportion of the positive emotion of the user is greater than or equal to a first threshold, determining the current emotion state of the user as a positive state;

when the proportion of the negative emotion of the user is greater than or equal to a second threshold, determining the current emotion state of the user as a negative state; and when both the proportions of the positive emotion and the negative emotion of the user are less than the second threshold and the proportion of the neutral emotion of the user is greater than or equal to a third threshold, determining the current emotion state of the user as a neutral state.

Preferably, the acquiring an emotion change state of the user based on an emotion proportion and a time change in each collection time period specifically includes:

taking the time change as an X value, taking the emotion proportion of the user in each collection time period as a Y value, and performing regression analysis using the X value and the Y value to obtain a slope;

acquiring a slope of the positive emotion and the negative emotion changing with time throughout the full-time history;

obtaining an emotion with the maximum slope change by comparison;

if the emotion with the maximum slope change is a descending negative emotion or an ascending positive emotion and the slope change is significantly not equal to 0, determining the emotion change state of the user as a positive change;

if the emotion with the maximum slope change is an ascending negative emotion or a descending positive emotion and the slope change is significantly different from 0, determining the emotion change state of the user as a negative change; and if the maximum slope change is not significantly distinguished from 0, determining the emotion change state of the user as no change.

Preferably, the acquiring an emotion fluctuation state of the user based on the emotion proportion and the time change in each collection time period specifically includes:

defining the emotion with the highest proportion in each collection time period as the current principal emotion component;

comparing the principal emotion components of two adjacent collection time periods, and analyzing whether the principal emotion component changes;

if the principal emotion component changes, recording as 1, otherwise, recording as 0;

calculating a principal emotion component change ratio in each task stage according to the record results of whether the principal emotion component changes; and if the principal emotion component change ratio is less than a fourth threshold, determining as a normal fluctuation, if the principal emotion component change ratio is greater than or equal to the fourth threshold and less than or equal to a fifth threshold, determining as a slight fluctuation, and if the principal emotion component change ratio is greater than the fifth threshold, determining as a severe fluctuation.

User information and user informed consent are acquired, the user informed consent including at least an evaluation content, a human-computer interaction content introduction, a user information collection range, and a user information usage range.

If the user agrees, cognitive evaluation is started and a face collection device is initiated to start collecting user expression data, and if the user disagrees, the evaluation is stopped.

According to a second aspect of embodiments of the present disclosure, a cognitive disorder human-computer interaction system based on emotion monitoring is provided, including:

an interaction unit, configured to receive information input by a user or output information to the user;

a storage unit, configured to store a computer program; and a processing unit, configured to read the computer program to execute the cognitive disorder human-computer interaction method.

The present disclosure has the following technical effects:

The present disclosure provides a cognitive disorder human-computer interaction method and system based on emotion monitoring. Cognitive evaluation and human-computer interaction tasks are mainly included, and a variety of basic emotion information of a user in the process of executing tasks is monitored simultaneously in real time, and an emotion comprehensive index of the user is obtained. Subsequent human-computer interaction tasks and states of the user are adjusted through the emotion comprehensive index, so as to achieve the purpose of improving the cognitive disorder human-computer interaction effect.

DETAILED DESCRIPTION

The technical content of the present disclosure is described in detail below with reference to the accompanying drawings and specific embodiments.

In the present disclosure, an open source emotion recognition package (real-time-emotion-detection-master) is used to capture expression data in real time by taking a period T (for example, 0.5 seconds) as a unit (with a variable value) after acquiring a face position of a user by a built-in or external face collection device, face features are analyzed, and six basic emotions: happiness, neutrality, sadness, anger, disgust, and surprise are obtained according to a comparison with an Asian face database. Each emotion has the following meanings:

Happiness: a positive emotion state in which the user is interest in human-computer interaction and the human-computer interaction is low in difficulty.

Neutrality: a calm and stable emotion state in which the user focuses on human-computer interaction and the human-computer interaction is moderate in difficulty.

Sadness: a depressed emotion state in which the user is immersed in the personal emotion and hardly enters into the human-computer interaction, or is self-denied due to high difficulty in human-computer interaction.

Anger: a disgusting and anxious emotion state in which the user is dissatisfied in human-computer interaction and the human-computer interaction is high in difficulty.

Disgust: an emotion state in which the user does not like the content of human-computer interaction and wants to avoid and end the human-computer interaction due to poor experience brought by the human-computer interaction.

Surprise: an emotion state in which the user goes into human-computer interaction, but the content or feedback of human-computer interaction is inconsistent with expectations, or the user does not understand the content of human-computer interaction and is slightly negative in the human-computer interaction scene.

In one embodiment of the present disclosure, the six different emotions are classified, where happiness belongs to positive emotions, neutrality belongs to neutral emotions, and sadness, anger, disgust, and surprise belong to negative emotions.

Figure 1:
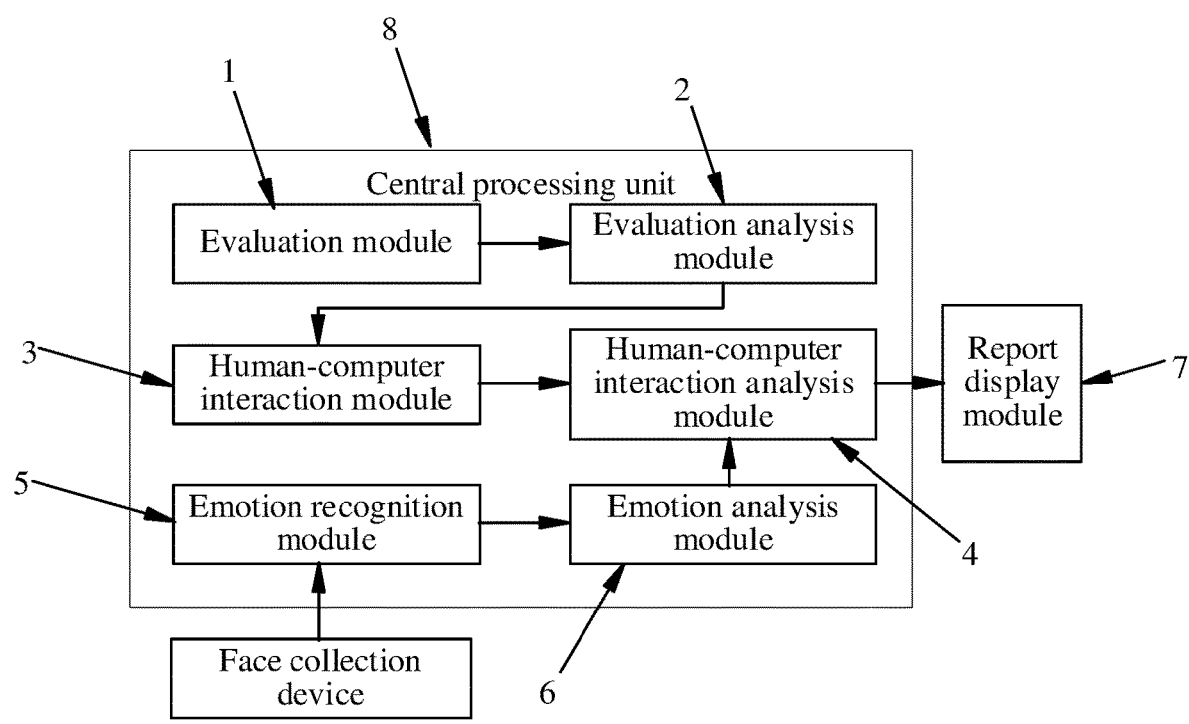
FIG. 1 is a schematic structural diagram of a cognitive disorder human-computer interaction system based on emotion monitoring according to an embodiment of the present disclosure.

FIG. 1 shows a cognitive disorder human-computer interaction system based on emotion monitoring according to an embodiment of the present disclosure. The system includes: an evaluation module 1, an evaluation analysis module 2, a human-computer interaction module 3, a human-computer interaction analysis module 4, an emotion recognition module 5, an emotion analysis module 6, a report display module 7, and a central processing unit 8.

The evaluation module 1 is connected to the central processing unit 8 and is configured to invoke a corresponding evaluation topic by means of human-computer interaction so as to carry out cognitive evaluation on a user. The evaluation and analysis module 2 is connected to the central processing unit 8 and is configured to carry out cognitive analysis on the user according to an answer result of the user so as to determine a cognitive impairment situation of the user. The human-computer interaction module 3 is connected to the central processing unit 8 and is configured to carry out human-computer interaction of cognitive tasks on the user according to the cognitive impairment situation of the user. The human-computer interaction analysis module 4 is connected to the central processing unit 8 and is configured to analyze a human-computer interaction situation of the user according to a human-computer interaction result of the user so as to determine whether the cognition of the user is improved. The emotion recognition module 5 is connected to the central processing unit 8, and is configured to capture a face expression of the user in real time during the evaluation process and the human-computer interaction process. The emotion analysis module 6 is connected to the central processing unit 8 (or connected to the emotion recognition module 5) and is configured to compare the captured user expressions with a face database so as to determine the emotion category of the user (i.e. belonging to one of positive, neutral or negative emotions). The report display module 7 is connected to the central processing unit 8 and is configured to output information, for example, display information such as the result of the cognitive evaluation of the user, the result of the human-computer interaction of the user and the emotion state of the user. The central processing unit 8 is configured to execute a cognitive disorder human-computer interaction method.

The cognitive disorder human-computer interaction method based on emotion monitoring provided by the present disclosure will be described in detail below:

First Embodiment

Figure 2:
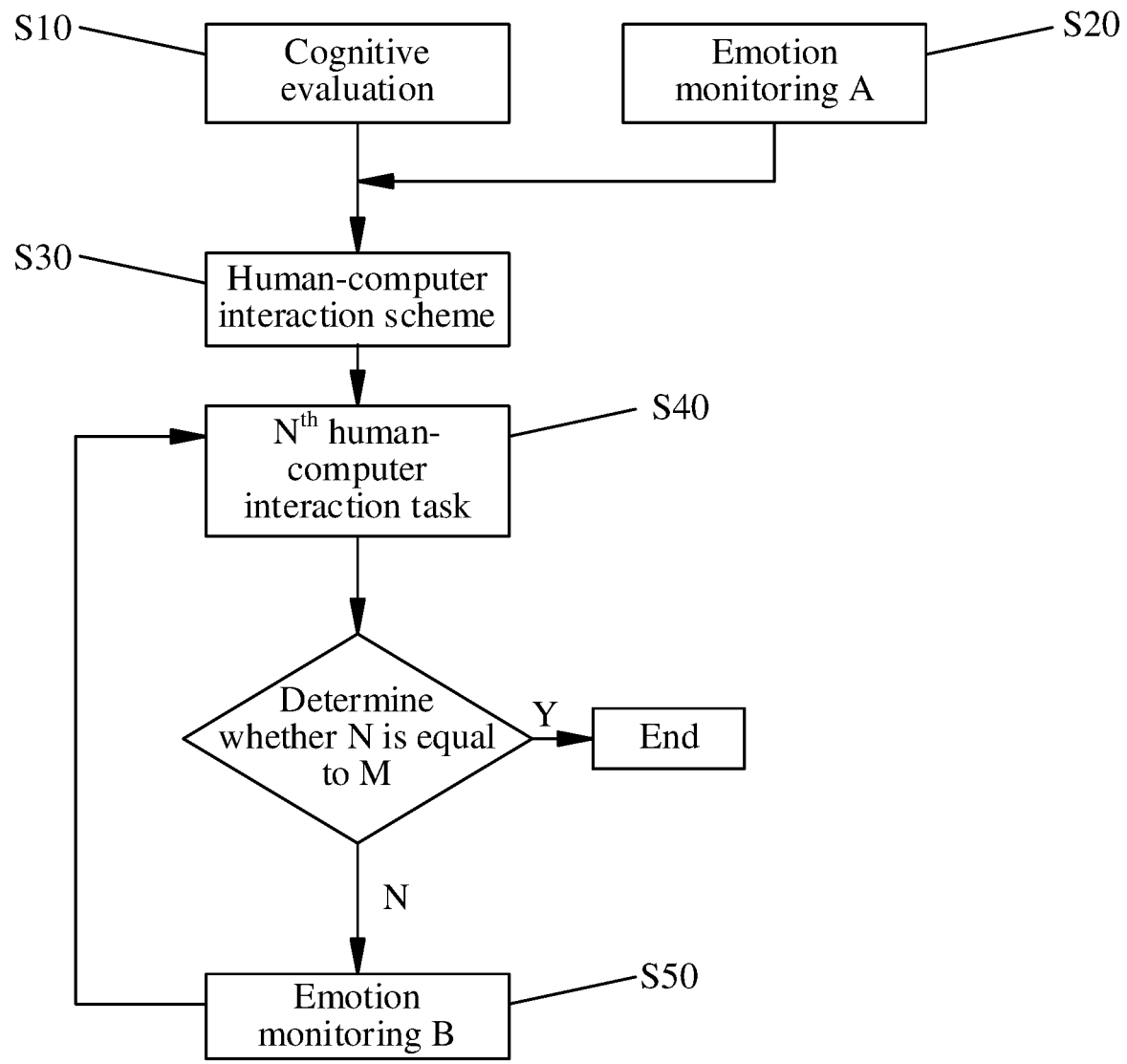
FIG. 2 is a flowchart of a cognitive disorder human-computer interaction method based on emotion monitoring according to an embodiment of the present disclosure.

FIG. 2 shows a cognitive disorder human-computer interaction method based on emotion monitoring according to this embodiment, which specifically includes the following steps:

S10: Obtain a cognitive ability level of a user

User information is acquired, and cognitive evaluation is carried out on the user according to an acquired evaluation topic, so as to obtain an evaluation result of the user.

Figure 3:
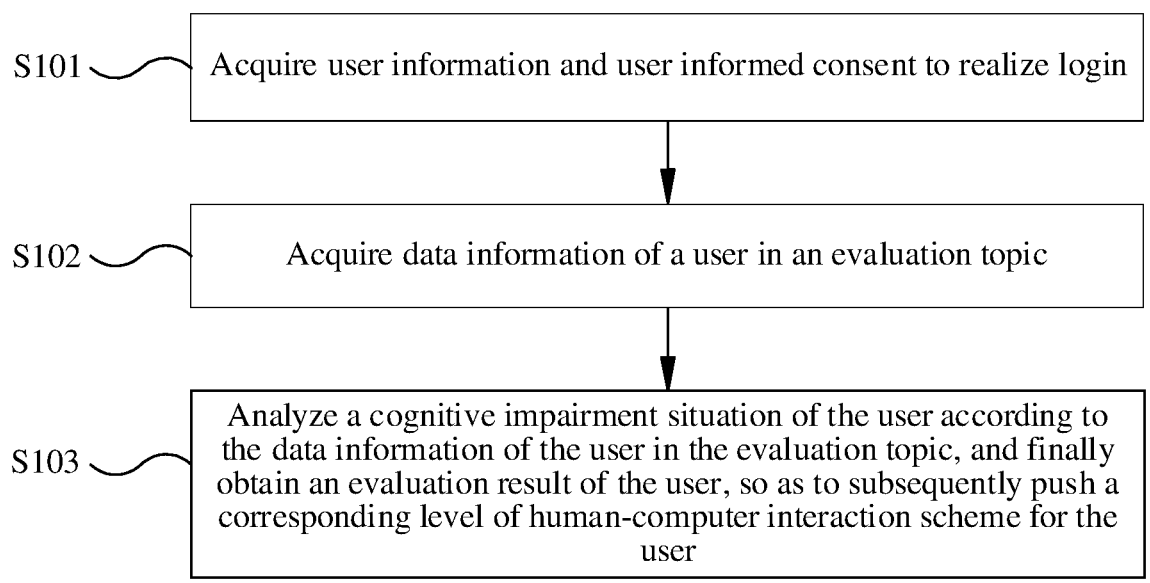
FIG. 3 is a flowchart of cognitive evaluation of a user.

As shown in FIG. 3, the operation specifically includes the following steps S101-S103:

S101: Acquire user information and user informed consent to realize login.

Specifically, the user needs to register an account in advance, and inputs personal information to obtain a login account, so as to log in a cognitive disorder human-computer interaction system. The user informed consent specifically includes: evaluation, a human-computer interaction content introduction, a user information collection range, a user information usage range, and other information. If the user agrees, cognitive evaluation is started and an emotion collection device is initiated to start collecting user expression data, and if the user disagrees, the evaluation is stopped.

It will be appreciated that this step may be omitted.

S102: Acquire data information of the user in an evaluation topic.

Specifically, when the user confirms to start the cognitive evaluation, the system invokes the corresponding evaluation topic from a database (for example: scales of different levels), the data information of the user in the evaluation topic is acquired according to an answer situation of the user for subsequent analysis.

S103: Analyze a cognitive impairment situation of the user according to the data information of the user in the evaluation topic, and finally obtain an evaluation result of the user, so as to subsequently push a corresponding level of human-computer interaction scheme for the user.

S20: Collect face information of the user to extract emotion information, and acquire an emotion comprehensive index of the user.

Figure 4:
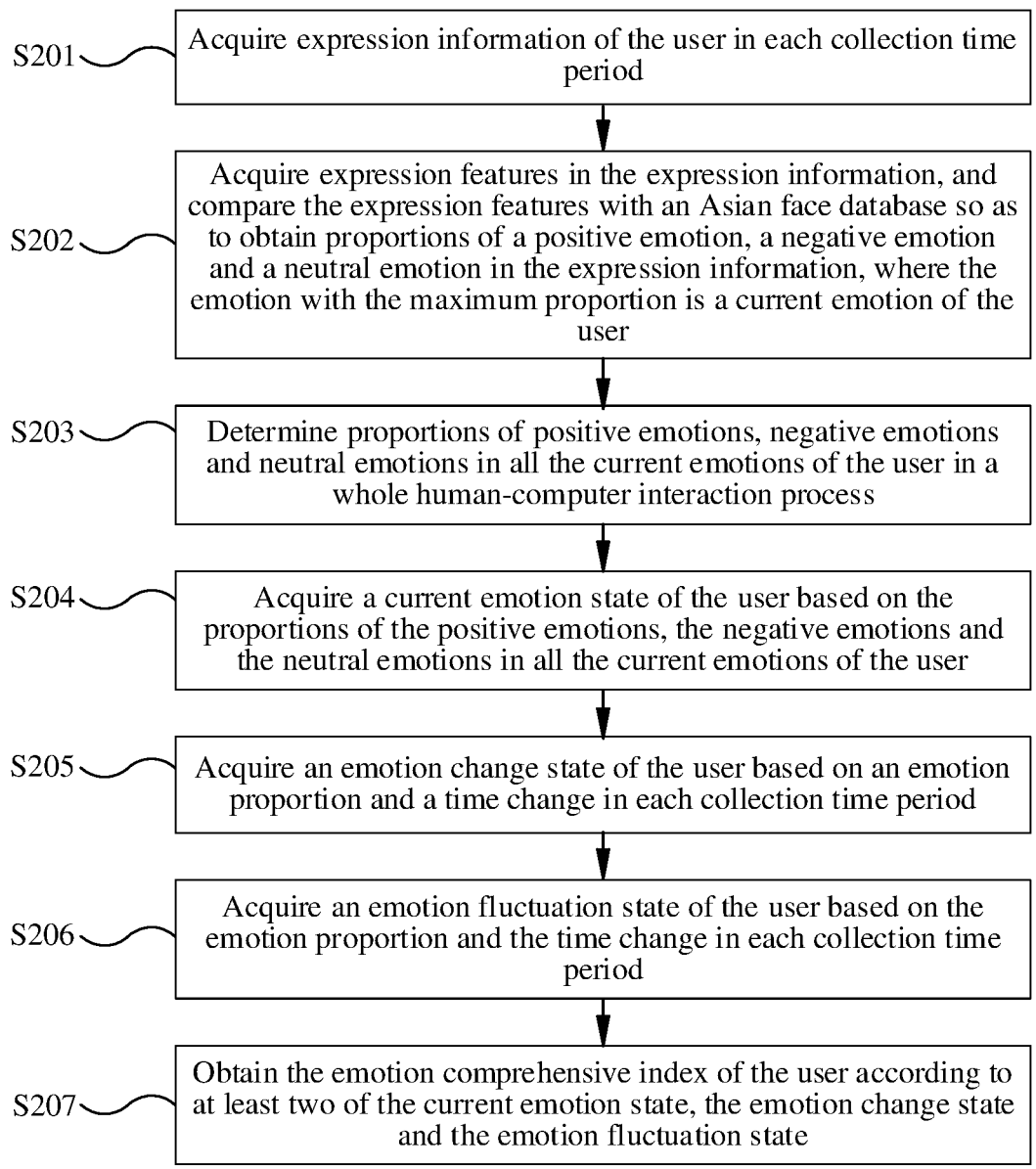
FIG. 4 is a flowchart of acquiring an emotion comprehensive index of a user.

As shown in FIG. 4, the operation specifically includes the following steps S201-S207: S201: Acquire expression information of the user in each collection time period.

In this embodiment, the expression information of the user is collected simultaneously during the cognitive evaluation of the user. Specifically, an open source emotion recognition package (real-time-emotion-detection-master) may be used to capture expression data in real time by 0.5 seconds as a collection time period (with a variable value) after acquiring a face position of the user by a built-in or external face collection device.

S202: Acquire expression features in the expression information, and compare the expression features with a face database so as to obtain similarity proportions of a positive emotion, a negative emotion and a neutral emotion in the expression information.

Specifically, in the form of a video stream, the software intercepts and captures the current expression information of each frame according to the face collection device in real time, analyzes expression emotion features using a cascade classifier based on Haar features, and compares the expression emotion features with six standard emotion models constructed by the face database (for example, an Asian face database) to obtain a standard similarity proportion of each emotion. The emotion with the maximum similarity proportion is a current emotion of the user. That is, the standard similarities of various emotions are calculated within a prescribed unit time, and the emotion with the highest similarity serves as the current emotion of the user. And then an emotion type of the user is determined according to the basic emotion (i.e. belonging to one of positive emotions, negative emotions and neutral emotions). For example, a collection time period is defined as 0.5 seconds, a picture transmission frame rate of a camera is 20 frames/second, and the software analyzes 10 frames of face emotions of the user in real time within the collection time period as shown in the following table, so as to obtain a happiness similarity of 0.65, a neutrality similarity of 0.19, a sadness similarity of 0.003, an anger similarity of 0.09, a disgust similarity of 0.0002, and a surprise similarity of 0.01. Then the user expression captured by the collection unit is happiness, and it is determined that the current emotion is a positive emotion.

The software analyzes 10 frames of face emotions of the user in real time within a collection time period as shown in Table 1:

TABLE 1

| Number of frames in unit | Anger | Disgust | Sadness | Happiness | Surprise | Neutrality |
|---|---|---|---|---|---|---|
| 1 | 0.082701 | 0.000300849 | 0.003102166 | 0.710286558 | 0.010221709 | 0.147617802 |
| 2 | 0.072682 | 0.000176214 | 0.00394929 | 0.796357155 | 0.018063443 | 0.080297284 |
| 3 | 0.042726111 | 5.40339E−05 | 0.001246092 | 0.747539997 | 0.003184185 | 0.166447029 |
| 4 | 0.082605027 | 0.000264138 | 0.004705108 | 0.490251958 | 0.015535718 | 0.298862606 |
| 5 | 0.118621536 | 0.000295937 | 0.003787976 | 0.403211385 | 0.013765618 | 0.352795094 |
| 6 | 0.144133478 | 0.0003543 | 0.003119486 | 0.450796932 | 0.025949353 | 0.273674965 |
| 7 | 0.083963729 | 0.000137187 | 0.003360974 | 0.630872965 | 0.023129571 | 0.186763853 |
| 8 | 0.036378726 | 0.000149024 | 0.005776993 | 0.901797056 | 0.012035174 | 0.031774726 |
| 9 | 0.106588304 | 0.000135205 | 0.004938024 | 0.728192329 | 0.014183545 | 0.109377623 |
| 10 | 0.113372497 | 0.000243247 | 0.003521722 | 0.613607347 | 0.008243959 | 0.205394134 |
| Average of this unit | 0.088377 | 0.000211 | 0.003751 | 0.647291 | 0.014431 | 0.185301 |

It will be appreciated that because the similarity proportion of each emotion is to compare the collected face expressions with the basic emotions individually, the face expressions of each user will have the proportions of positive emotions, negative emotions and neutral emotions, but the sum of proportions of positive emotions, negative emotions and neutral emotions is not necessarily equal to 1. After the comparative analysis, the emotion with the maximum similarity proportion is found as the current emotion of the user under the face expressions.

S203: Calculate proportions of positive emotions, negative emotions and neutral emotions of the user within a collection time.

Within the time range of a cognitive evaluation stage or a human-computer interaction stage, by determining all the current emotions of the user within a collection time, the number of positive emotions, the number of negative emotions and the number of neutral emotions of the user are obtained within the time period. Then, the proportions of positive emotions, negative emotions and neutral emotions are calculated according to the total amount of the current emotions within the collection time. For example, in the cognitive evaluation stage, the user takes 5 minutes for cognitive evaluation, and then the face collection device obtains 600 current emotions of the user within the 5 minutes. If there are 300 positive emotions, 200 negative emotions and 100 neutral emotions among the 600 current emotions, the proportion of the positive emotions is 50%, the proportion of the negative emotions is 33.3%, and the proportion of the neutral emotions is 16.7%.

S204: Acquire a current emotion state of the user based on the proportions of the positive emotions, the negative emotions and the neutral emotions in all the current emotions of the user.

Figure 5:
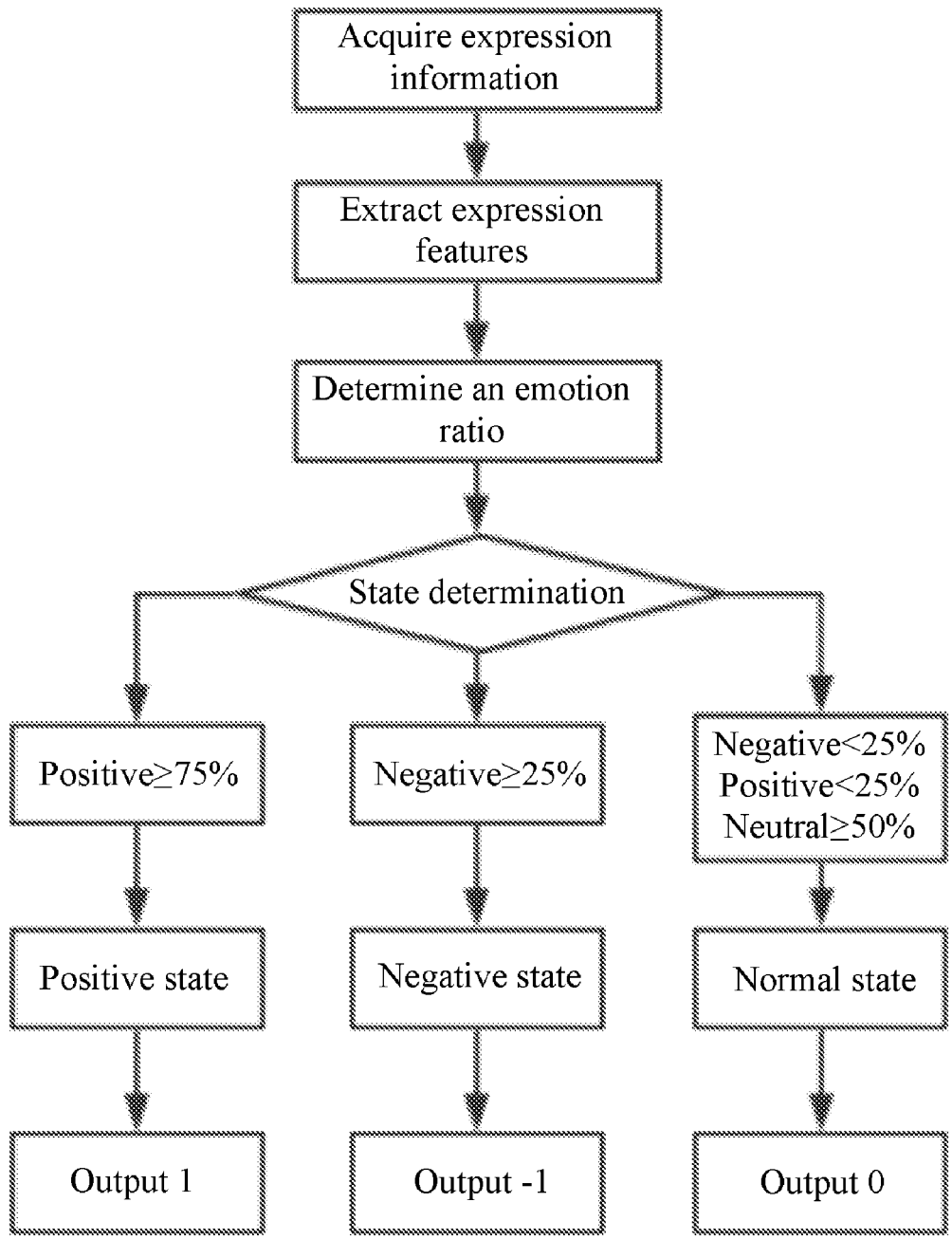
FIG. 5 is a qualitative flowchart of acquiring a current emotion state.

Referring to FIG. 5, when the emotion proportion of the user is obtained, the current emotion state of the user is defined using a percentage average of the emotions. When the proportion of the positive emotion of the user is greater than or equal to 75% (i.e. first threshold), the current emotion state of the user is a positive state. At this moment, the output result of the emotion analysis module 6 is 1, indicating that the value of the emotion state is 1. When the proportion of the negative emotion of the user is greater than or equal to 25% (i.e. second threshold), the current emotion state of the user is a negative state. At this moment, the output result of the emotion analysis module 6 is −1, indicating that the value of the emotion state is −1. When both the proportions of the positive emotion and the negative emotion of the user are less than 25% and the proportion of the neutral emotion of the user is greater than or equal to 50% (i.e. third threshold), the current emotion state of the user is a neutral state. At this moment, the output result of the emotion analysis module 6 is 0, indicating that the value of the emotion state is 0.

For example, in the above example, if the proportion of the negative emotion is 33.3%, the current emotion state of the user is a negative state, and the output result of the emotion analysis module 6 is −1.

Those skilled in the art will appreciate that the reason to divide negative 25% from positive 75% is that the psychological perception is that negative and positive feelings of subjective feelings of a person have a weight difference of about 3:1, and three positive feelings are needed to cancel one negative feeling. However, the above values have different sizes according to different populations. For example, in the evaluation process for children, when the ratio of the positive emotion is greater than or equal to 80% (i.e. the threshold is increased), it is determined that the value of the emotion state is 1 since the positive emotion of normal children is greater than that of adults. Similarly, in the case of the evaluation of the elderly, when the ratio of the positive emotion is greater than or equal to 70% (i.e. the threshold is reduced), it is determined that the value of the emotion state is 1. Different thresholds may also be set depending on gender or race.

S205: Acquire an emotion change state of the user based on an emotion proportion and a time change in each collection time period.

Figure 6:
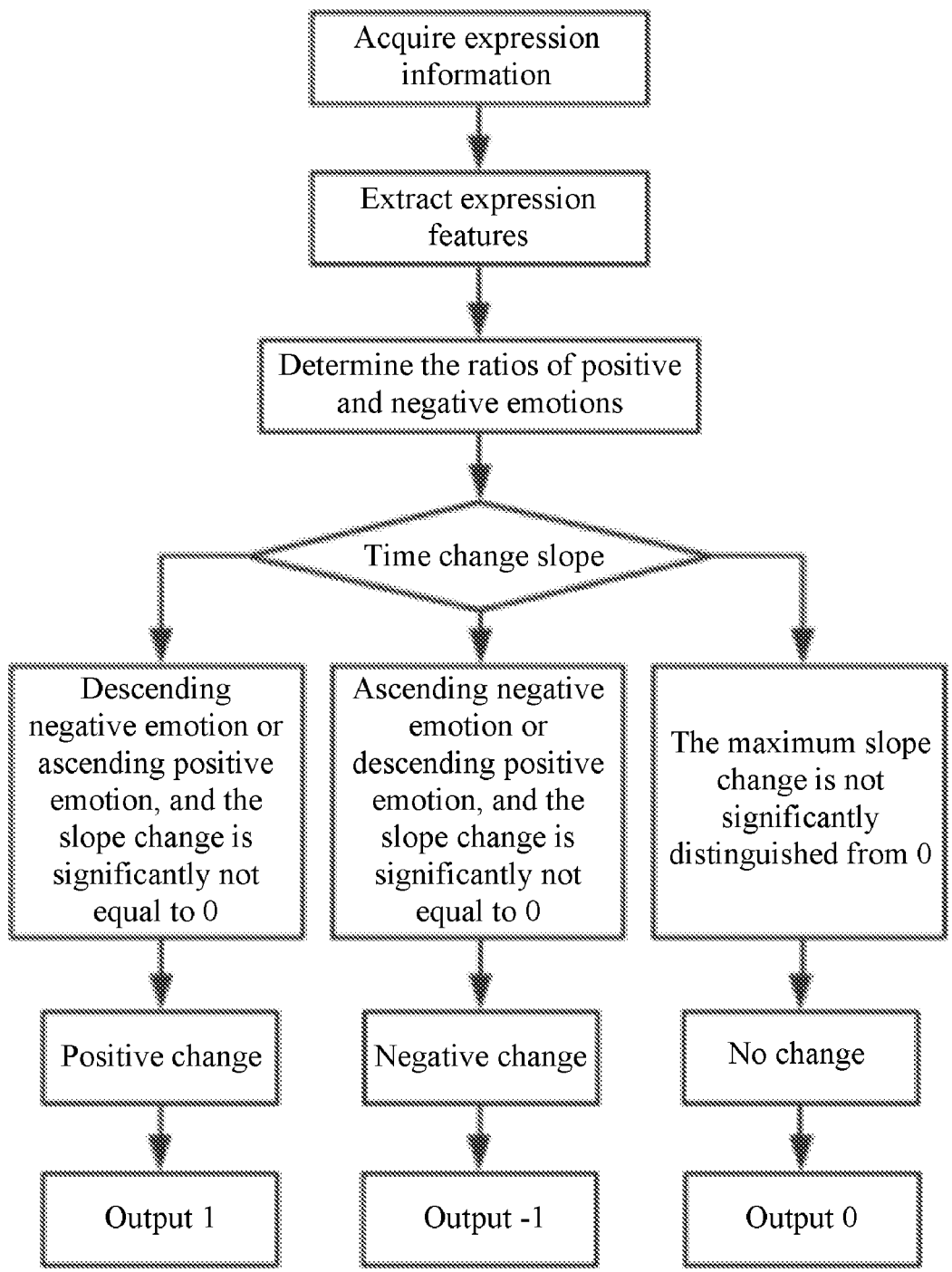
FIG. 6 is a qualitative flowchart of acquiring an emotion change state.

Referring to FIG. 6, for example, taking 500 ms as a collection time period, it can be seen from reference to step S201 that the user expression collected in the collection time period needs to be compared with six basic emotions respectively, so as to obtain the proportions of positive emotions, negative emotions and neutral emotions in each collection time period.

The formulas show that the face collection device captures x expressions of the user, and obtains a proportion (y1) of positive emotions and a proportion (y2) of negative emotions in each collection. Regression analysis (x and y1, x and y2) is carried out on the proportions of positive emotions and negative emotions, respectively, using a time frequency to obtain normalized regression coefficients (b1, b2) as slopes and significance parameters (p1, p2) as significance references for statistical significance. If p corresponds to max (|b1|, |b2|) is less than 0.05, |b1| and |b2| are compared. If |b1|>|b2| and b1>0, or |b1|<|b2| and b2<0, a positive change is made. If |b1|>|b2| and b1<0, or |b1|<|b2| and b2>0, a negative change is made. If p corresponds to max (|b1|, |b2|) is greater than 0.05, there is no change.

For example, the duration of a task is 120 seconds, and the face collection device captures 240 expressions of user (x), and obtains a proportion (y1) of positive emotions and a proportion (y2) of negative emotions in each of 240 collections. Regression analysis (x and y1, x and y2) is carried out on the proportions of positive emotions and negative emotions, respectively, using a time frequency. If the positive emotions are calculated: b1=0.25, p1=0.03, and negative emotions are: b2=−0.38, p1=0.01, p2<0.05, |b1|<|b2|, b2<0, the negative emotions are significantly reduced, a positive change is made, and the system output result is 1. If the positive emotions are calculated: b1=−0.28, p1=0.02, and negative emotions are: b2=−0.04, p1=0.64, p1<0.05, |b1|>|b2|, b1<0, the positive emotions are significantly reduced, a negative change is made, and the system output result is −1. If the positive emotions are calculated: b1=−0.12, p1=0.32, and negative emotions are: b2=0.04, p1=0.44, p1>0.05, neither the positive nor negative emotion is significantly changed, there is no change, and the system output result is 0.

It will be appreciated that a larger slope represents a greater increase in emotions over time. For example, positive emotions are the greatest increase in slope, which means that the user feels happier when performing more tasks. A slope of the positive emotion and the negative emotion changing with time throughout the full time history is acquired based on the emotion proportion situation of the user throughout the full time history. Then, an emotion with the maximum slope change is obtained by comparison.

If the emotion with the maximum slope change is a descending negative emotion or an ascending positive emotion and the slope change is significantly not equal to 0, the emotion change state of the user is a positive change, and at this moment, the system output result is 1. If the emotion with the maximum slope change is an ascending negative emotion or a descending positive emotion and the slope change is significantly not equal to 0, the emotion change state of the user is a negative change, and at this moment, the system output result is −1. If the maximum slope change is not significantly distinguished from 0, the emotion change state of the user is no change, and at this moment, the system output result is 0.

It will be appreciated that the neutral emotion is not considered in the slope change because it is difficult to define from which part or where the change of the neutral emotion comes, it is meaningful to compare the neutral emotion rather than considering the meaning of the change of the neutral emotion departing from the positive and negative emotions.

S206: Acquire an emotion fluctuation state of the user based on the emotion proportion and the time change in each collection time period.

Figure 7:
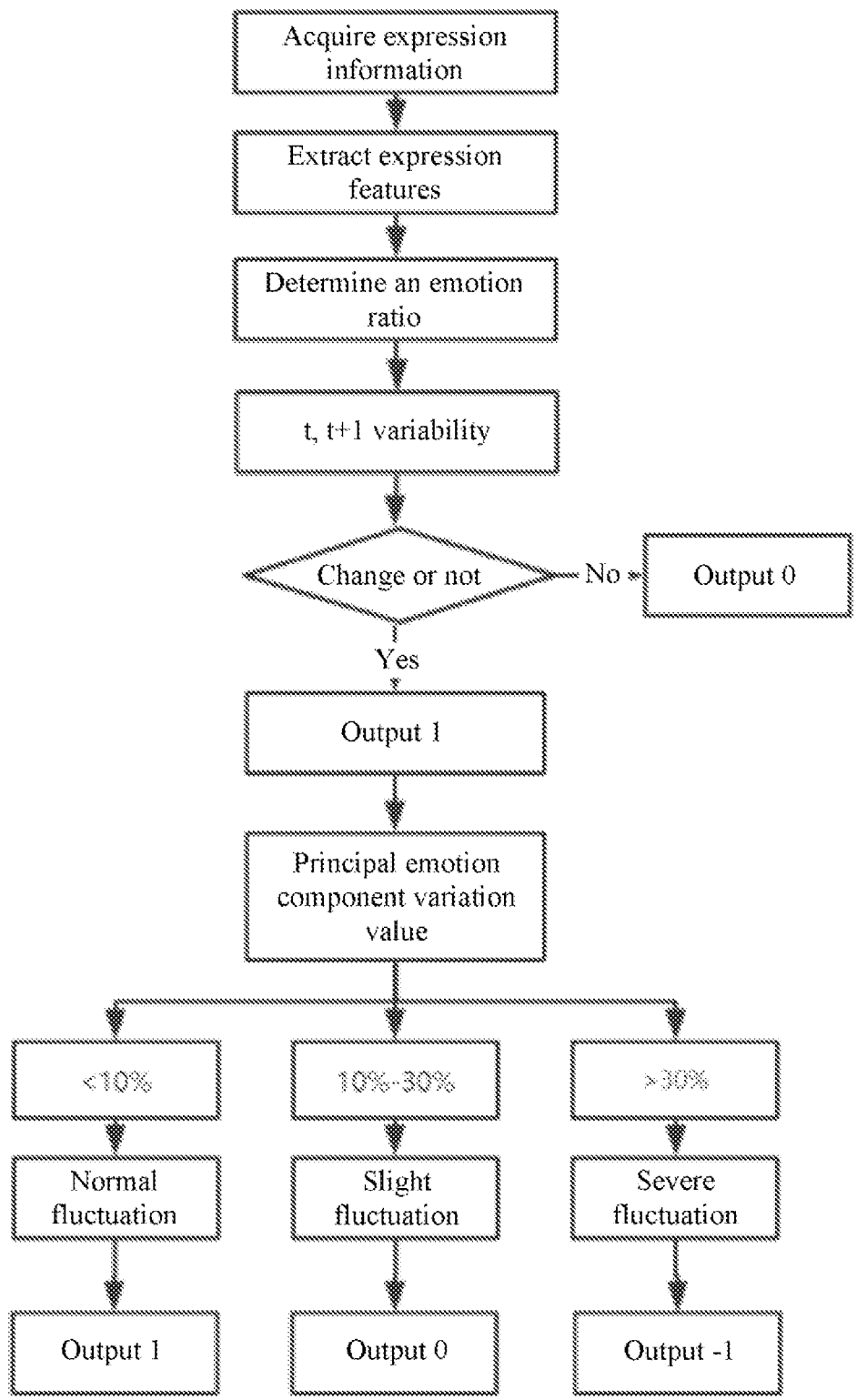
FIG. 7 is a qualitative flowchart of acquiring an emotion fluctuation state.

As shown in FIG. 7, the emotion with the highest similarity proportion when recorded in each collection time period is defined as the current principal emotion component, referring to steps S201-S202:

The principal emotion components of two adjacent collection time periods are compared, and it is analyzed whether the principal emotion component changes.

If the principal emotion component changes, it is recorded as 1, otherwise, it is recorded as 0.

A principal emotion component change ratio in each task stage is calculated according to the record results of whether the principal emotion component changes.

If the principal emotion component change ratio is less than 10% (i.e. fourth threshold), there is a normal fluctuation, and at this moment, the system output result is 1. If the principal emotion component change ratio is greater than or equal to 10% and less than or equal to 30% (i.e. fifth threshold), there is a slight fluctuation, and at this moment, the system output result is 0. If the principal emotion component change ratio is greater than 30%, there is a severe fluctuation, and at this moment, the system output result is −1.

For example, the duration of a certain task is 75 seconds. When the principal emotion component of 56 seconds changes, the variability is 56/75=74.7%, and the ratio of non-variability is 25.3%. Since 74.7% is greater than 30%, it is determined that the emotion fluctuation of the user is severe, and the system output result is −1.

It will be appreciated that in one embodiment of the present disclosure, 10% and 30% are defined from the system evaluating the user. The collected face data is subjectively evaluated by tens of users thereafter whether the emotion is in no fluctuation/slight fluctuation/severe fluctuation, and the current objective face emotion change rate is calculated. It is concluded that the boundary between no fluctuation and slight fluctuation is the principal emotion component change ratio of 10%, and the boundary between slight fluctuation and severe fluctuation is the principal emotion component change ratio of 30%.

S207: Obtain the emotion comprehensive index of the user according to at least two of the current emotion state, the emotion change state and the emotion fluctuation state.

Figure 8:
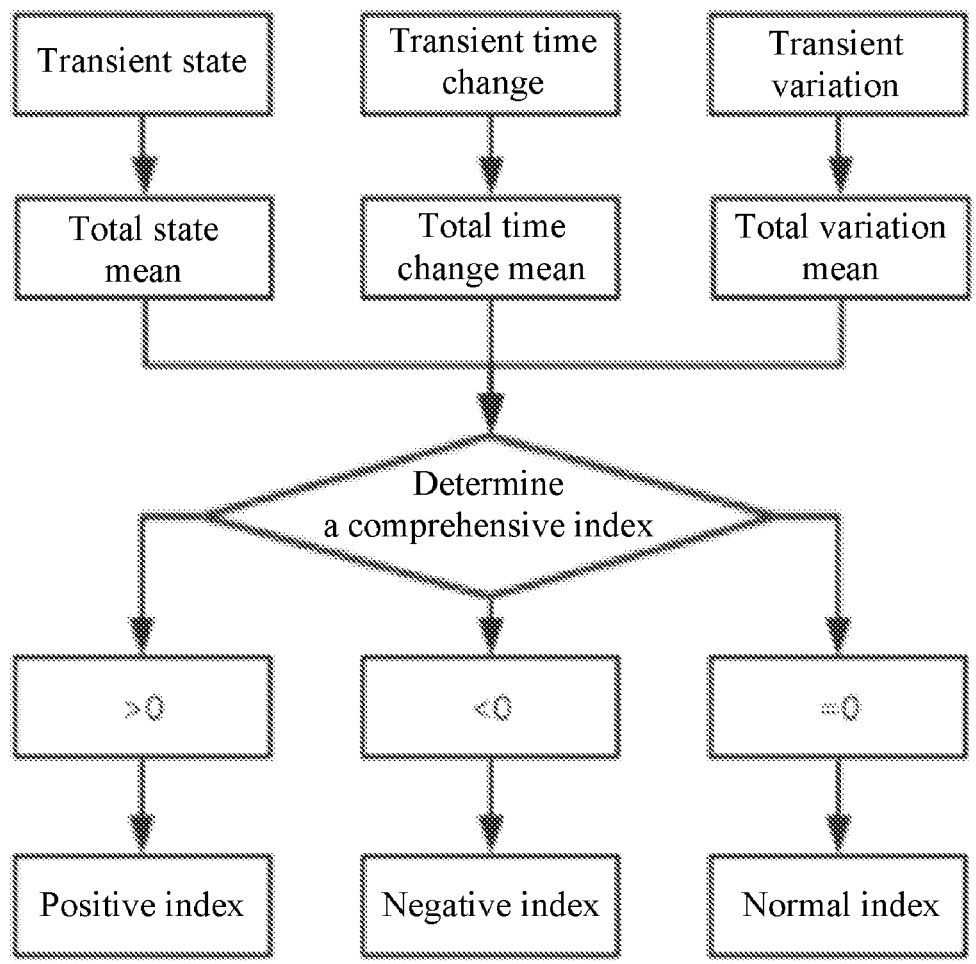
FIG. 8 is a qualitative flowchart of acquiring an emotion comprehensive index.

As shown in FIG. 8, the system output results of the current emotion state, the emotion change state and the emotion fluctuation state are added to obtain an emotion comprehensive index of the user, and the emotion situation of the user can be determined according to the emotion comprehensive index of the user in accordance with the following specific determination criteria:

If the sum of the three output results is greater than 0, the emotion comprehensive index is positive, and the system output emotion comprehensive index is 1. If the three output results are less than 0, the emotion comprehensive index is negative, and the system output emotion comprehensive index is −1. If the three output results are equal to 0, the emotion comprehensive index is neutral, and the system output emotion comprehensive index is 0.

For example, the current emotion state of the user is a positive state, and the system output result is 1. The emotion change state of the user is a negative change state, and the system output result is −1. The emotion fluctuation state of the user is a normal fluctuation, the system output result is 1, and then the emotion comprehensive index is equal to 1+(−1)+1=1>0. Therefore, the emotion comprehensive index of the user is positive. At this moment, the emotion comprehensive index is obtained by integrating the current emotion state, the emotion change state and the emotion fluctuation state. In another example, the current emotion state of the user is a positive state, and the system output result is 1. The emotion change state of the user is a negative change state, and the system output result is −1. Then the emotion comprehensive index is equal to 1+(−1)=0. Therefore, the emotion comprehensive index of the user is neutral. At this moment, the emotion comprehensive index is obtained by integrating the current emotion state, the emotion change state and the emotion fluctuation state. In another example, the emotion change state of the user is a negative change state, and the system output result is −1. The emotion fluctuation state of the user is a severe fluctuation, the system output result is −1, and then the emotion comprehensive index is equal to (−1)+(−1)=−2<0. The emotion comprehensive index of the user is negative. At this moment, the emotion comprehensive index is obtained by integrating the emotion change state and the emotion fluctuation state. In another example, the current emotion state of the user is a positive state, and the system output result is 1. The emotion fluctuation state of the user is a normal fluctuation, the system output result is 1, and then the emotion comprehensive index is equal to 1+1=2>0. Therefore, the emotion comprehensive index of the user is positive. At this moment, the emotion comprehensive index is obtained by integrating the current emotion state and the emotion fluctuation state.

It will be appreciated that in one embodiment of the present disclosure, the determination accuracy of the emotion comprehensive index can be improved by using the current emotion state, the emotion change state and the emotion fluctuation state as the determination basis, and in other embodiments, any two of the current emotion state, the emotion change state and the emotion fluctuation state may be selected to be combined to determine the emotion comprehensive index.

In addition, in another embodiment, different weights may be given to the current emotion state, the emotion change state and the emotion fluctuation state. Then, the emotion comprehensive index of the user may be calculated by weighting, and the emotion comprehensive index of the user may be calculated in a manner not limited to the above addition of the three output results.

S30: Acquire a human-computer interaction scheme of the user according to the evaluation result and the emotion comprehensive index.

Specifically, when the cognitive evaluation of the user is completed, the cognitive impairment level of the user is determined according to the evaluation result, and the human-computer interaction task level of the user is jointly determined according to the emotion comprehensive index (i.e. emotion monitoring A) of the user in the evaluation process.

For example, after the user completes the evaluation (i.e. after completing step S10), the system provides a comprehensive evaluation level of the brain ability of the user according to the norm standard of each task: good, mild and severe, and an emotion comprehensive index in the evaluation process: positive, neutral and negative. After acquiring the results of the two indexes, the human-computer interaction scheme level is selected, and a higher level represents a more difficult human-computer interaction task.

The specific selection rule may be seen in Table 2:

TABLE 2

| Determine human-computer interaction task level comprehensively through emotion-brain ability | | Comprehensive evaluation level of brain ability | | |
|---|---|---|---|---|
| | | Good | Mild | Severe |
| Emotion comprehensive index | Positive | High-order | High-order | Medium-order |
| | Neutral | High-order | Medium-order | Low-order |
| | Negative | Medium-order | Low-order | Low-order |

It will be appreciated that the difficulty coefficient of the human-computer interaction scheme is increased in sequence from a low order to a high order, and the number and types of human-computer interaction tasks included in the human-computer interaction schemes of different orders are different. For example, the low-order human-computer interaction scheme may include 3-5 simple human-computer interaction tasks, the medium-order human-computer interaction scheme may include 4-6 medium human-computer interaction tasks, and the high-order human-computer interaction scheme may include 5-8 difficult human-computer interaction tasks, whereby the most suitable human-computer interaction scheme can be selected according to the situation of different users.

S40: Obtain an emotion comprehensive index after the human-computer interaction according to the emotion monitoring of the user in completing the human-computer interaction task, and obtain a human-computer interaction result of the user.

Specifically, after a corresponding equal-order human-computer interaction scheme is generated for the user, the system will push an initial human-computer interaction task, and when the user carries out the human-computer interaction, the system will record the process of the human-computer interaction during the task completion so as to collect human-computer interaction data, thereby acquiring the human-computer interaction result of the user. Meanwhile, in the process of completing the human-computer interaction task, the face expression is collected by the face collection device, whereby the emotion comprehensive index is analyzed (i.e. emotion monitoring B) by the method described in step 20, so as to obtain the emotion comprehensive index of the user in the process of completing the human-computer interaction task. It will be appreciated that both emotion monitoring A and emotion monitoring B are the analysis of the emotion comprehensive index through step 20, except that the timing of the emotion monitoring is different. Emotion monitoring A is the emotion monitoring on the user when the user carries out the evaluation, and emotion monitoring B is the emotion monitoring on the user when the user carries out the human-computer interaction task.

S50: Calculate and push the next human-computer interaction task according to the human-computer interaction result and the emotion comprehensive index after the human-computer interaction until all the tasks in the human-computer interaction scheme are completed.

Specifically, M (M is a positive integer, similarly hereinafter) human-computer interaction tasks are included in a human-computer interaction scheme. Starting from an initial human-computer interaction task (i.e. N=1), it is determined whether the number N (N is a positive integer, similarly hereinafter) of human-computer interaction tasks that have been completed is equal to M. If N is equal to M, the human-computer interaction scheme ends. If N is less than M, the next human-computer interaction task (i.e. N=2) is pushed through the human-computer interaction result of the previous human-computer interaction task and the emotion comprehensive index of the user in the previous human-computer interaction task. After the second human-computer interaction scheme is completed, it is determined whether N is equal to M again, and the operations are successively circulated until N=M, thereby completing the whole human-computer interaction scheme.

When calculating the next human-computer interaction task, if the emotion comprehensive index is negative, the task difficulty is reduced, and if the human-computer interaction result is good, the task difficulty is upgraded.

The specific pushing plan is shown with reference to Table 3:

TABLE 3

| Emotion-human-computer | Emotion comprehensive index | | |
|---|---|---|---|
| interaction regulation | Positive 1 | Normal 0 | Negative −1 |
| Human-computer interaction result | Good 1 | Upgrade | Upgrade | Reduce pushing, update |

TABLE 3-continued

| Emotion-human-computer | Emotion comprehensive index | | |
|---|---|---|---|
| interaction regulation | Positive 1 | Normal 0 | Negative −1 |
| interaction result | Moderate 0 | Increase pushing | Maintain | Reduce pushing |
| | Poor −1 | Increase pushing, degrade | Degrade | Degrade |

In this embodiment, the human-computer interaction result is divided into good, moderate and poor, and the emotion comprehensive index is divided into positive, normal and negative. Meanwhile, it will be appreciated that pushing is increased and reduced aiming at human-computer interaction tasks of the same level, and the number of human-computer interaction tasks is increased or reduced. Upgrading or degrading represents the increase or reduction of the difficulty level of the human-computer interaction task.

When the human-computer interaction result is good, task pushing is successively carried out according to upgrade, upgrade, and reduce pushing and upgrade in the order of the emotion comprehensive index being positive, normal and negative.

When the human-computer interaction result is moderate, task pushing is successively carried out according to increase pushing, maintain, and reduce pushing in the order of the emotion comprehensive index being positive, normal and negative.

When the human-computer interaction result is poor, task pushing is successively carried out according to increase pushing and degrade, degrade, and degrade in the order of the emotion comprehensive index being positive, normal and negative.

In summary, the embodiments of the present disclosure provide a cognitive disorder human-computer interaction method based on emotion monitoring. Cognitive evaluation and human-computer interaction tasks are mainly included, and a variety of basic emotion information of a user in the process of executing tasks is monitored simultaneously in real time, and an emotion comprehensive index of the user is obtained. Subsequent human-computer interaction tasks and states of the user are adjusted through the emotion comprehensive index, so as to achieve the purpose of improving the cognitive disorder human-computer interaction effect.

Second Embodiment

Figure 9:
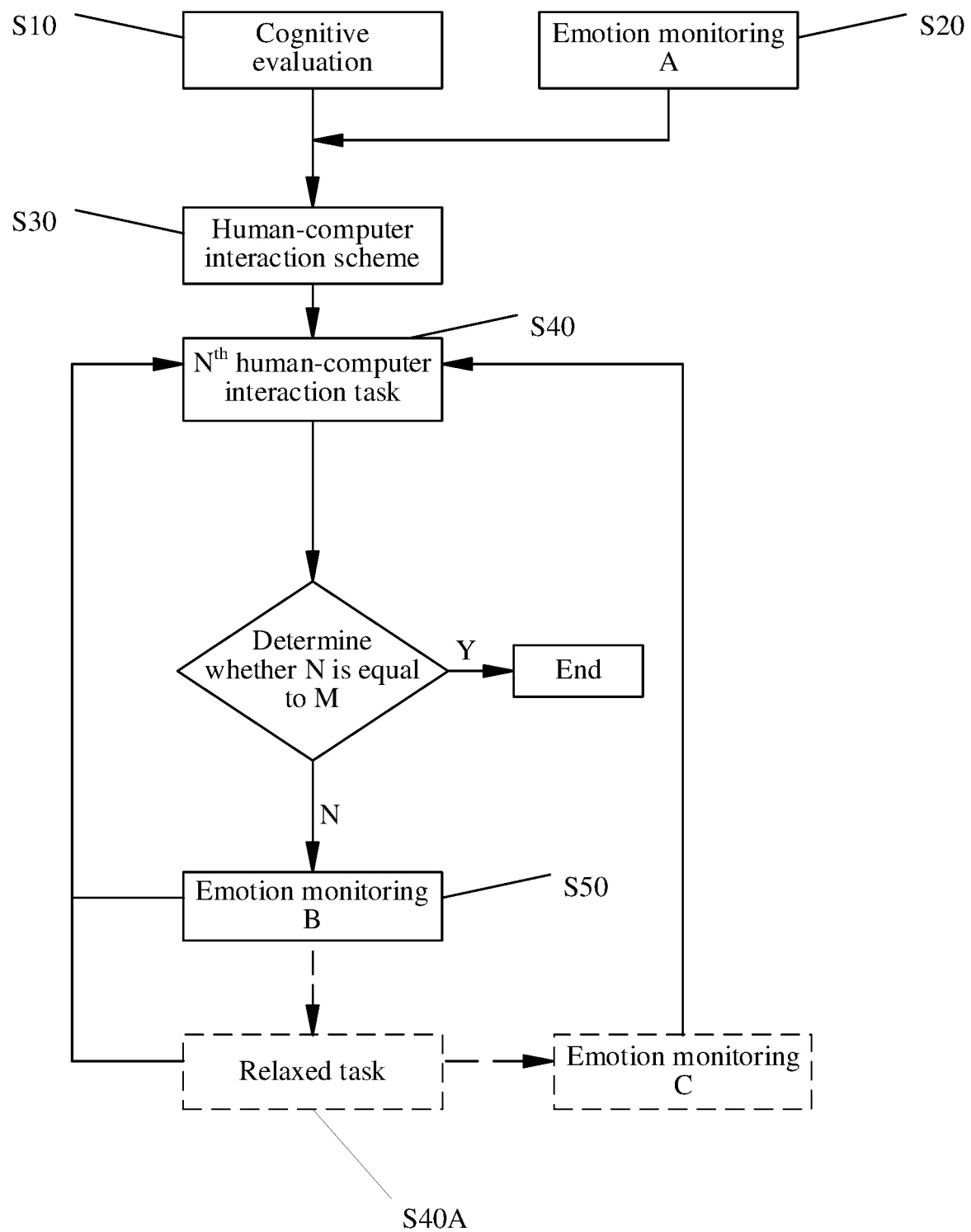
FIG. 9 is a flowchart of another cognitive disorder human-computer interaction method based on emotion monitoring according to an embodiment of the present disclosure.

As shown in FIG. 9, after step S40, the above-mentioned cognitive disorder human-computer interaction method further includes the following steps:

S40A: Carry out, in the process of human-computer interaction, a relaxed human-computer interaction between two adjacent human-computer interaction tasks, and select a task type of the relaxed human-computer interaction according to an emotion comprehensive index of the user in the previous human-computer interaction task.

The specific selection rule is shown with reference to Table 4:

TABLE 4

| Emotion comprehensive index | Relaxed task selection rule |
| --- | --- |
| Positive index | High strength challenge class |
| Negative index | High relaxation and stress relief class |
| Neutral index | Random selection |

When the emotion comprehensive index is positive, a human-computer interaction task of a high strength challenge class is selected, when the emotion comprehensive index is negative, a human-computer interaction task of a high relaxation and stress relief class is selected, and when the emotion comprehensive index is neutral, a human-computer interaction task is randomly selected from the foregoing two tasks. It will be appreciated that in this embodiment, the task of the high strength challenge class refers to a task with a higher difficulty level and requiring the user to complete with own efforts, and the task of the high relaxation and stress relief class refers to a task with a lower difficulty level and being easily completed by the user.

It will be appreciated that the existence of step S40A is specifically determined according to the actual situation. When a human-computer interaction task is completed once, it is necessary to determine whether the whole human-computer interaction scheme is completed (i.e. whether N is equal to M). If the whole human-computer interaction scheme is not completed (i.e. N is not equal to M), step S40A is executed to push the relaxed interaction task.

If the whole human-computer interaction scheme is completed, it is not necessary to carry out the relaxed interaction task. For example, a human-computer interaction scheme includes a plurality of human-computer interaction tasks (i.e. M>1), and then the whole interaction process is: a mode of human-computer interaction-relaxed interaction-human-computer interaction-relaxed interaction. If a human-computer interaction scheme includes only one human-computer interaction task (i.e. M=1), there is no relaxed interaction mode.

Meanwhile, in this embodiment, emotion monitoring (i.e. emotion monitoring C) is also carried out when the user carries out relaxed interaction. It will be appreciated that the steps of emotion monitoring during relaxed interaction are the same as the steps of emotion monitoring A and emotion monitoring B, except that the monitoring timing of emotion monitoring C is when the user carries out relaxed interaction. However, emotion monitoring of relaxed interaction is only used to ensure that the user relaxes successfully and does not serve as a push basis for the next human-computer interaction task. The pushing of the next human-computer interaction task is based on the human-computer interaction result of the previous human-computer interaction task and the emotion comprehensive index (i.e. emotion monitoring B) during the previous human-computer interaction task.

Third Embodiment

Figure 10:
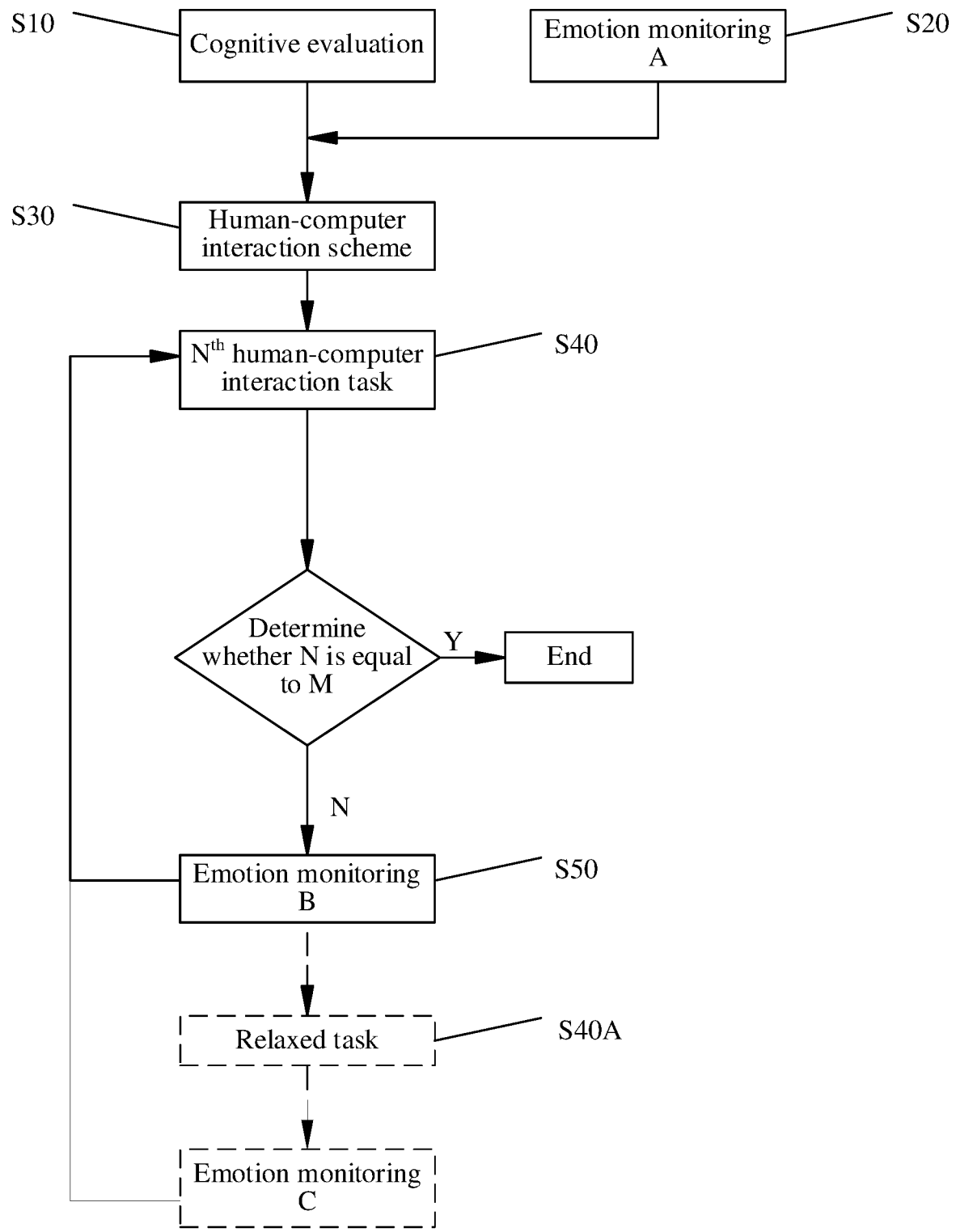
FIG. 10 is a flowchart of yet another cognitive disorder human-computer interaction method based on emotion monitoring according to an embodiment of the present disclosure.

Referring to FIG. 10, this embodiment differs from the second embodiment in that in this embodiment, emotion monitoring is carried out when a user carries out a relaxed interaction (i.e. emotion monitoring C). Meanwhile, an emotion comprehensive index obtained during the relaxed interaction is taken as a push basis for the next human-computer interaction task.

Specifically, in this embodiment, after the previous human-computer interaction task is completed, the user will enter a relaxed interaction mode. In the process of relaxed interaction, an emotion comprehensive index of the user in the process of relaxed interaction is obtained by carrying out emotion monitoring (i.e. emotion monitoring C) on the user. Finally, the next human-computer interaction task is pushed in cooperation with the emotion comprehensive index of the user in the process of relaxed interaction according to the human-computer interaction result of the previous human-computer interaction task of the user, and this loop is continued until the whole human-computer interaction scheme is completed.

Fourth Embodiment

As shown in FIG. 2, this embodiment includes the following steps:

S10': Obtain a cognitive ability level of a user.

S30': Generate a human-computer interaction scheme according to the cognitive ability level.

S40': Generate an $N^{th}$ human-computer interaction task according to the human-computer interaction scheme.

S50': Carry out emotion monitoring on the performance of the user in the $N^{th}$ human-computer interaction task.

S60': Adjust the human-computer interaction scheme generated in S30' based on the result of emotion monitoring to generate a new human-computer interaction scheme, and return to S40' of generating an $N^{th}$ human-computer interaction task according to the new human-computer interaction scheme, whereby N=N+1 until all M tasks in the new human-computer interaction scheme are completed.

The cognitive ability level in step S10' may be obtained based on a conventional cognitive ability evaluation method, or using a near-infrared brain imaging map of the brain, etc.

The human-computer interaction scheme generated in S30' is adjusted based on the result of emotion monitoring in step S60'.

Figure 11:
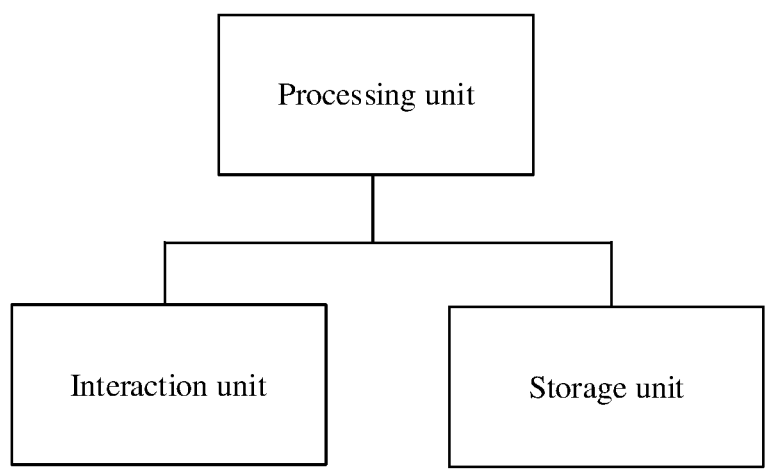
FIG. 11 is a schematic structural diagram of another cognitive disorder human-computer interaction system based on emotion monitoring according to an embodiment of the present disclosure.

As shown in FIG. 11, an embodiment of the present disclosure also provides another cognitive disorder human-computer interaction system based on emotion monitoring, including: an interaction unit, a storage unit and a processing unit. The system may be a server and a plurality of communication terminals (for example, personal computers, tablet computers or mobile phones, etc.), and may also be a computer or a mobile phone, etc.

The interaction unit communicates with the processing unit and is configured to receive information input by a user or output information to the user. The interaction unit may be a keyboard and a display, and may also be an input/output component of a smart phone or a tablet computer.

The storage unit is electrically connected to the processing unit for storing an associated computer program for executing the human-computer interaction method provided by the present disclosure. Therefore, data associated with the human-computer interaction and evaluation, etc. of the user may be retrieved repeatedly. The storage unit may be a hard disk in a computer, or a U disk, or a storage component of a smart phone or a tablet computer.

The processing unit may be a central processing unit of a computer or a processor of a smart phone or tablet computer, and is configured to read the computer program to execute the cognitive disorder human-computer interaction method provided by the embodiments of the present disclosure.

The cognitive disorder human-computer interaction method and system based on emotion monitoring provided in the present disclosure are described in detail above. For a person of ordinary skill in the art, any obvious modifications made to the present disclosure without departing from the essence of the present disclosure will constitute an infringement of patent rights of the present disclosure, and corresponding legal liabilities will be born.

What is claimed is:

1. A cognitive disorder human-computer interaction method based on emotion monitoring, comprising the following steps:
    obtaining a cognitive ability level of a user;
    generating a human-computer interaction scheme according to the cognitive ability level;
    generating an Nth human-computer interaction task according to the human-computer interaction scheme, N being a positive integer;
    carrying out emotion monitoring on the performance of the user in the Nth human-computer interaction task, and returning to the previous step of generating an Nth human-computer interaction task according to the human-computer interaction scheme, whereby N=N+1 until all tasks in the human-computer interaction scheme are completed; and
    carrying out, in the process of human-computer interaction, a relaxed human-computer interaction between two adjacent human-computer interaction tasks, and selecting a task type of the relaxed human-computer interaction according to an emotion comprehensive index of the user in the previous human-computer interaction task, wherein when the emotion comprehensive index is positive, a human-computer interaction task of a high strength challenge class is selected; when the emotion comprehensive index is negative, a human-computer interaction task of a high relaxation and stress relief class is selected; and when the emotion comprehensive index is neutral, a human-computer interaction task is randomly selected;
    wherein the emotion comprehensive index being obtained by the following steps:
    acquiring expression information of the user in each collection time period;
    acquiring expression features in the expression information, and comparing the expression features with an Asian face database so as to obtain proportions of a positive emotion, a negative emotion and a neutral emotion in the expression information, the emotion with the maximum proportion being a current emotion of the user;
    determining proportions of positive emotions, negative emotions and neutral emotions in all the current emotions of the user in the whole process of human-computer interaction;
    acquiring a current emotion state of the user based on the proportions of the positive emotions, the negative emotions and the neutral emotions in all the current emotions of the user;
    acquiring an emotion change state of the user based on an emotion proportion and a time change in each collection time period;
    acquiring an emotion fluctuation state of the user based on the emotion proportion and the time change in each collection time period; and
    obtaining the emotion comprehensive index of the user according to at least two of the current emotion state, the emotion change state and the emotion fluctuation state.

2. The cognitive disorder human-computer interaction method according to claim 1, wherein
    when the user completes the relaxed human-computer interaction, the next human-computer interaction task is pushed according to a human-computer interaction result of the previous human-computer interaction task and the emotion comprehensive index of the user after the relaxed human-computer interaction.

3. The cognitive disorder human-computer interaction method according to claim 1, wherein
    the human-computer interaction result is divided into good, moderate and poor, and the emotion comprehensive index is divided into positive, normal and negative;
    when the human-computer interaction result is good, task pushing is successively carried out according to upgrade, upgrade, and reduce pushing and upgrade in the order of the emotion comprehensive index being positive, normal and negative;
    when the human-computer interaction result is moderate, task pushing is successively carried out according to increase pushing, maintain, and reduce pushing in the order of the emotion comprehensive index being positive, normal and negative; and
    when the human-computer interaction result is poor, task pushing is successively carried out according to increase pushing and degrade, degrade, and degrade in the order of the emotion comprehensive index being positive, normal and negative.

4. The cognitive disorder human-computer interaction method according to claim 1, wherein the acquiring a current emotion state of the user based on the proportions of the positive emotions, the negative emotions and the neutral emotions in all the current emotions of the user specifically comprises:
    when the proportion of the positive emotion of the user is greater than or equal to a first threshold, determining the current emotion state of the user as a positive state;
    when the proportion of the negative emotion of the user is greater than or equal to a second threshold, determining the current emotion state of the user as a negative state; and
    when both the proportions of the positive emotion and the negative emotion of the user are less than the second threshold and the proportion of the neutral emotion of the user is greater than or equal to a third threshold, determining the current emotion state of the user as a neutral state.

5. The cognitive disorder human-computer interaction method according to claim 1, wherein the acquiring an emotion change state of the user based on an emotion proportion and a time change in each collection time period specifically comprises:
    taking the time change as an X value, taking the emotion proportion of the user in each collection time period as a Y value, and performing regression analysis using the X value and the Y value to obtain a slope;
    acquiring a slope of the positive emotion and the negative emotion changing with time throughout the full time history;
    obtaining an emotion with the maximum slope change by comparison;
    if the emotion with the maximum slope change is a descending negative emotion or an ascending positive emotion and the slope change is significantly not equal to 0, determining the emotion change state of the user as a positive change;
    if the emotion with the maximum slope change is an ascending negative emotion or a descending positive emotion and the slope change is significantly not equal to 0, determining the emotion change state of the user as a negative change; and if the maximum slope change is not significantly distinguished from 0, determining the emotion change state of the user as no change.

6. The cognitive disorder human-computer interaction method according to claim 1, wherein the acquiring an emotion fluctuation state of the user based on the emotion proportion and the time change in each collection time period specifically comprises:

defining the emotion with the highest proportion in each collection time period as the current principal emotion component;

comparing the principal emotion components of two adjacent collection time periods, and analyzing whether the principal emotion component changes;

if the principal emotion component changes, recording as 1, otherwise, recording as 0;

calculating a principal emotion component change ratio in each task stage according to the record results of whether the principal emotion component changes; and if the principal emotion component change ratio is less than a fourth threshold, determining as a normal fluctuation, if the principal emotion component change ratio is greater than or equal to the fourth threshold and less than or equal to a fifth threshold, determining as a slight fluctuation, and if the principal emotion component change ratio is greater than the fifth threshold, determining as a severe fluctuation.

7. The cognitive disorder human-computer interaction method according to claim 1, wherein user information and user informed consent are acquired, the user informed consent comprising at least an evaluation content, a human-computer interaction content introduction, a user information collection range, and a user information usage range; and if the user agrees, cognitive evaluation is started and a face collection device is initiated to start collecting user expression data, and if the user disagrees, the evaluation is stopped.

8. A cognitive disorder human-computer interaction system based on emotion monitoring, comprising:

an interaction unit, configured to receive information input by a user or output information to the user;

a storage unit, configured to store a computer program; and a processing unit, configured to read the computer program to execute the cognitive disorder human-computer interaction method according to claim 1.

* * * * *